(12) United States Patent
Nakashima et al.

(10) Patent No.: US 10,517,501 B2
(45) Date of Patent: Dec. 31, 2019

(54) ELECTROENCEPHALOGRAM ANALYSIS APPARATUS AND ELECTROENCEPHALOGRAM ANALYSIS METHOD

(71) Applicant: SONY CORPORATION, Tokyo (JP)

(72) Inventors: Yusaku Nakashima, Tokyo (JP); Takashi Tomita, Kanagawa (JP); Masaki Nishida, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/938,144

(22) Filed: Mar. 28, 2018

(65) Prior Publication Data

US 2018/0214043 A1    Aug. 2, 2018

Related U.S. Application Data

(63) Continuation of application No. 13/602,703, filed on Sep. 4, 2012, now abandoned.

(30) Foreign Application Priority Data

Apr. 5, 2012 (JP) ................................. 2012-086588

(51) Int. Cl.
*A61B 5/0476* (2006.01)
*A61B 5/048* (2006.01)
(Continued)

(52) U.S. Cl.
CPC ............ *A61B 5/048* (2013.01); *A61B 5/0476* (2013.01); *A61B 5/165* (2013.01); *A61B 5/4812* (2013.01);
(Continued)

(58) Field of Classification Search
None
See application file for complete search history.

(56) References Cited

U.S. PATENT DOCUMENTS 5,230,346 A    7/1993   Leuchter et al.
6,477,408 B1   11/2002  Turek et al.
(Continued)

FOREIGN PATENT DOCUMENTS

JP    62-253034 A    11/1987
JP    11-276449 A    10/1999
(Continued)

OTHER PUBLICATIONS

Armitage, Roseanne, R. F. Hoffmann, and A. J. Rush. "Biological rhythm disturbance in depression: temporal coherence of ultradian sleep EEG rhythms." Psychological medicine 29.6 (1999): 1435-1448.*

(Continued)

*Primary Examiner* — Patricia Mallari
*Assistant Examiner* — Jairo H Portillo
(74) *Attorney, Agent, or Firm* — Chip Law Group

(57) ABSTRACT

An electroencephalogram analysis apparatus includes an electroencephalogram acquisition part and a comparison part. The electroencephalogram acquisition part is configured to acquire a first electroencephalogram measured at a first region on a head of a test subject and a second electroencephalogram measured at a second region positioned behind the first region on the head of the test subject. The comparison part is configured to compare a power of the first electroencephalogram in a specific frequency band with a power of the second encephalogram in the specific frequency band.

9 Claims, 10 Drawing Sheets

(51) Int. Cl.
*A61B 5/16* (2006.01)
*A61B 5/00* (2006.01)
*A61B 5/04* (2006.01)
*A61B 5/0488* (2006.01)

(52) U.S. Cl.
CPC ......... *A61B 5/04012* (2013.01); *A61B 5/0488* (2013.01)

(56) References Cited

U.S. PATENT DOCUMENTS

| | | |
|---|---|---|
| 7,177,675 B2 | 2/2007 | Suffin et al. |
| 8,538,512 B1 | 7/2013 | Bibian et al. |
| 2003/0181821 A1 | 9/2003 | Greenwald et al. |
| 2006/0235315 A1 | 10/2006 | Akselrod et al. |
| 2007/0060831 A1* | 3/2007 | Le ................ A61B 5/0476 600/544 |
| 2008/0195166 A1* | 8/2008 | Sun ................ A61B 5/0478 607/18 |
| 2011/0015503 A1 | 1/2011 | Joffe et al. |
| 2013/0218043 A1* | 8/2013 | Yoshida .......... A61B 5/04012 600/544 |

FOREIGN PATENT DOCUMENTS

| | | |
|---|---|---|
| JP | 2009-518076 A | 5/2009 |
| WO | 2010/123577 A2 | 10/2010 |

OTHER PUBLICATIONS

Ferrarelli, Fabio, et al. "Thalamic dysfunction in schizophrenia suggested by whole-night deficits in slow and fast spindles." American Journal of Psychiatry 167.11 (2010): 1339-1348.*

Higashima, Masato, et al. "State-dependent changes in intrahemispheric EEG coherence for patients with acute exacerbation of schizophrenia." Psychiatry research 149.1-3 (2007): 41-47.*

Nakamura, Motoaki, et al. "Sleep spindles in human prefrontal cortex: an electrocorticographic study." Neuroscience research 45.4 (2003): 419-427.*

Fogel, et al., "The Function of the Sleep spindle: A Physiological Index of Intelligence and a Mechanism for Sleep-Dependent Memory Consolidation", Neuroscience & Biobehavioral Reviews, vol. 35, Issue 5, Apr. 2011, pp. 1154-1165.

Tamaki, et al., "Fast Sleep Spindle (13-15 Hz) Activity Correlates with Sleep-Dependent Improvement in Visuomotor Performance", Sleep and Performance, vol. 31, Issue 2,2008, pp. 204-211.

John P. John, "Fronto-Temporal Dysfunction in Schizophrenia: A Selective Review", Indian Journal of Psychiatry, vol. 51, Issue 3, Jul.-Sep. 2009, 17 pages.

Fogel, et al., The Function of the Sleep Spindle: A Physiological Index of Intelligence and a Mechanism for Sleep-Dependent Memory Consolidation, Neuroscience and Biobehavioral Reviews, 35, Dec. 9, 2010, pp. 1154-1165.

Tamaki, et al., "Fast Sleep Spindle (13-15Hz) Activity Correlates with Sleep-Dependent Improvement in Visuomotor Performance", 2008, Sleep, vol. 31, pp. 204-211.

Final-Office Action for U.S. Appl. No. 13/602,703, dated Dec. 26, 2017, 34 pages.

Non-Final Office Action for U.S. Appl. No. 13/602,703, dated Apr. 6, 2017, 28 pages.

Final-Office Action for U.S. Appl. No. 13/602,703, dated Nov. 18, 2016, 21 pages.

Non-Final-Office Action for U.S. Appl. No. 13/602,703, dated Apr. 20, 2016, 19 pages.

Advisory Action for U.S. Appl. No. 13/602,703, dated Feb. 26, 2016, 03 pages.

Final Office Action for U.S. Appl. No. 13/602,703, dated Nov. 6, 2015, 15 pages.

Non-Final Office Action for U.S. Appl. No. 13/602,703, dated Jun. 5, 2015, 16 pages.

John, John P. "Fronto-temporal dysfunction in schizophrenia: A selective review." Indian journal of psychiatry 51.3 (2009): 180.

* cited by examiner

FIG.4

| Sleep stage | | State | Characteristics |
|---|---|---|---|
| Non-sleep | WAKE | Wake | EEG:Alpha waves and waves of low amplitudes and high frequency components are mixed together<br>EMG:Waves of high amplitudes and persistence<br>EOG:REM(Rapid Eye Movement) |
| REM sleep | REM | REM sleep | EEG:Alpha waves gradually decrease with time<br>EOG:REM<br>EMG:Lowest amplitudes |
| Non-REM sleep | STAGE1 | Hypnagogic | EEG:Alpha waves gradually decrease with time<br>EOG:SEM(Slow Eye Movement) |
| Non-REM sleep | STAGE2 | Light sleep | EEG:Sleep spindles, K complex waves, no high amplitude slow waves exist, less than or equal to 20% of delta waves<br>EOG、EMG:Persistently emerge, low amplitudes |
| Non-REM sleep | STAGE3 | Moderate sleep | EEG:20 to 50% of delta waves (less than or equal to 2 Hz and less than or equal to 75 $\mu V$)<br>EMG: Waves of lower amplitudes and more persistence than that of waves of STAGE 2 |
| Non-REM sleep | STAGE4 | Deep sleep | EEG:Greater than or equal to 50% of delta waves (less than or equal to 2 Hz and less than or equal to 75 $\mu V$)<br>EMG:Same as STAGE 3 |

First electroencephalogram spectrum

Mood disorder state (first region)

Second electroencephalogram spectrum

Mood disorder state (second region)

First electroencephalogram spectrum
Normal state (first region)

Second electroencephalogram spectrum
Normal state (second region)

Mood disorder state
Slow sleep spindle (10.5Hz～12.5Hz)

Normal state
Slow sleep spindle (10.5Hz～12.5Hz)

Mood disorder state
Slow sleep spindle (10.5Hz~12.5Hz)

Normal state
Slow sleep spindle (10.5Hz~12.5Hz)

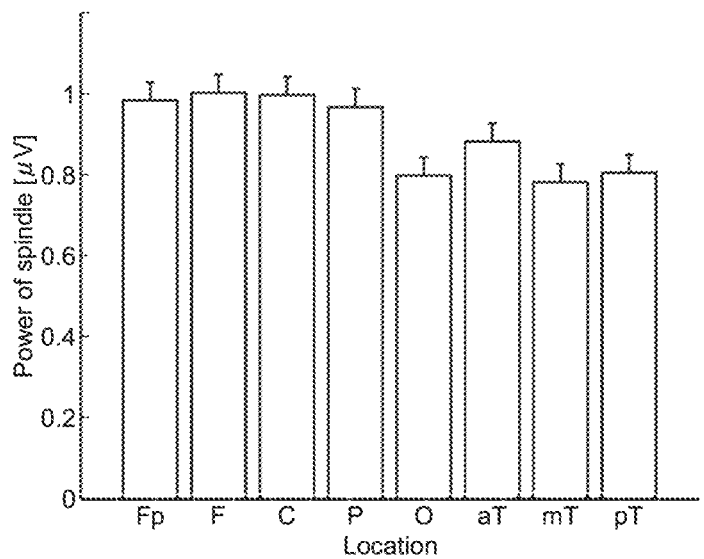
Mood disorder state
Fast sleep spindle (12.5Hz~16Hz)
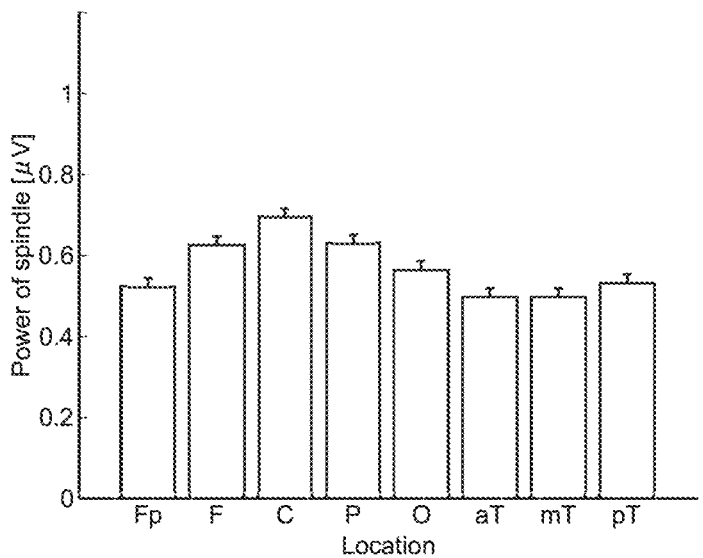
Normal state
Fast sleep spindle (12.5Hz~16Hz)

Mood disorder state

Fast sleep spindle (12.5Hz~16Hz)

Normal state

Fast sleep spindle (12.5Hz~16Hz)

though the patients are in a wakeful state, thus making it possible for patients to judge the mood disorders by themselves.

ELECTROENCEPHALOGRAM ANALYSIS APPARATUS AND ELECTROENCEPHALOGRAM ANALYSIS METHOD

CROSS REFERENCE TO RELATED APPLICATIONS

This application is a continuation application of U.S. patent application Ser. No. 13/602,703, filed Sep. 4, 2012 and which claims the benefit of Japanese Priority Patent Application JP 2012-086588 filed Apr. 5, 2012, the entire contents of which are incorporated herein by reference.

BACKGROUND

The present disclosure relates to an electroencephalogram analysis apparatus, an electroencephalogram analysis program, and an electroencephalogram analysis method for analyzing electroencephalograms measured at the head of a test subject.

Mood disorders such as depression, schizophrenia, and bipolar disorder (symptom where a depressed state and a manic state alternately appear) cannot be diagnosed from the physical symptoms of patients. Therefore, clinical methods such as asking patients about their conditions are generally conducted to diagnose such mood disorders. Meanwhile, it is difficult for patients to judge such mood disorders by themselves, and the patients are thus likely to lose opportunities to consult doctors at the early stages of the disorders. It is assumed that the availability of any clear barometers indicating such mood disorders facilitates the judgement of the mood disorders, thus making it possible for patients to judge the mood disorders by themselves.

In recent years, there have been developed technologies for diagnosing mood disorders such as depression based on electroencephalograms (electrical activities of the brain of a human). For example, Japanese Patent Application Laid-open No. 2009-518076 discloses a "system and method of analyzing and evaluating depression and other mood disorders using electroencephalogram (EEG) measurement values." The system allows the evaluation of the mood disorders based on the results of electroencephalograms measured when test subjects are in a wakeful state (i.e. in a non-sleep state), more specifically, based on the asymmetry of right and left front qEEGs (quantitative electroencephalograms).

SUMMARY

The system described in Japanese Patent Application Laid-open No. 2009-518076 is used to evaluate the mood disorders based on the results of the electroencephalograms measured when the patients are in the wakeful state. Therefore, the patients have to take time for measuring the electroencephalograms in their daily lives and may be forced to bear the burden of measuring the electroencephalograms. Meanwhile, the present inventors have found characteristics indicating the mood disorders in the electroencephalograms measured during sleep states and achieved a method of evaluating the mood disorders using the characteristics.

The present disclosure has been made in view of the above circumstances, and it is therefore desirable to provide an electroencephalogram analysis apparatus, an electroencephalogram analysis program, and an electroencephalogram analysis method capable of diagnosing mood disorders based on the electroencephalograms of a test subject.

According to an embodiment of the present disclosure, there is provided an electroencephalogram analysis apparatus including an electroencephalogram acquisition part and a comparison part.

The electroencephalogram acquisition part is configured to acquire a first electroencephalogram measured at a first region on a head of a test subject and a second electroencephalogram measured at a second region positioned behind the first region on the head of the test subject.

The comparison part is configured to compare a power of the first electroencephalogram in a specific frequency band with a power of the second encephalogram in the specific frequency band.

The present inventors have found a difference in the distribution of the powers of the electroencephalograms in the specific frequency band, particularly on the front and rear sides of the head, between a mood disorder state and a normal state. Accordingly, it is possible to diagnose whether the test subject is in the mood disorder state by the comparison between the power of the electroencephalogram in the specific frequency band measured at the first region and that of the electroencephalogram in the specific frequency band measured at the second region, the first region and the second region being positioned on the front and rear sides of the head of the test subject, respectively. In other words, the electroencephalogram analysis apparatus with the above configuration makes it possible to diagnose whether the test subject is in the mood disorder state.

In the electroencephalogram analysis apparatus, the first region may be a prefrontal region, and the second region may be a frontal region.

It has been found as the distribution of the powers of the electroencephalograms in the specific frequency band that the power of the electroencephalogram on the front side (frontal region) of the head becomes the greatest when the test subject is in the normal state and that the power of the electroencephalogram on the further front side (prefrontal region) of the head becomes the greatest when the test subject is in the mood disorder state. Accordingly, it is possible to more clearly detect the difference in the distribution of the powers between the mood disorder state and the normal state by setting the prefrontal region as the first region and the frontal region as the second region.

The first region may be an Fp region defined based on the International 10-20 system, and the second region may be an F region defined based on the International 10-20 system.

The prefrontal region corresponds to the Fp region (Fp1, Fpz, or Fp2) based on the definition of the International 10-20 system, and the frontal region corresponds to the F region (Fz or F1 to F9) based on the definition of the International 10-20 system.

The specific frequency band is a frequency band of sleep spindles.

It has been confirmed that the difference in the distribution of the powers occurs at least in the frequency band (generally, greater than or equal to 10.5 Hz and less than or equal to 16 Hz) of the sleep spindles. Accordingly, by setting the frequency band of the sleep spindles as the specific frequency band, it is possible to diagnose whether the test subject is in the mood disorder state based on the electroencephalograms measured at the first region and the second region.

The sleep spindles are classified into slow sleep spindles and fast sleep spindles. The difference in the distribution of the powers between the mood disorder state and the normal state can be notably seen in the slow sleep spindles. Therefore, it is possible to diagnose whether the test subject is in the mood disorder state by setting the frequency band of the slow sleep spindles as the specific frequency band.

The frequency band of the slow sleep spindles may be greater than or equal to 10.5 Hz and less than or equal to 12.5 Hz.

The frequency band of the slow sleep spindles is generally greater than or equal to 10.5 Hz and less than or equal to 12.5 Hz in the field of electroencephalogram measurement.

The electroencephalogram analysis apparatus may further include a stage discrimination part configured to discriminate a sleep stage of the test subject. The first electroencephalogram may be an electroencephalogram of any of sleep stages 2 to 4 measured at the first region, and the second electroencephalogram may be an electroencephalogram of any of the sleep stages 2 to 4 measured at the second region.

Electroencephalograms (such as alpha waves) occurring when the test subject is not in a sleep state may overlap with the specific frequency, resulting in a difficulty in diagnosing whether the test subject is in the mood disorder state. According to the configuration, the stage discrimination part discriminates the sleep stage of the test subject. Therefore, it is possible to diagnose whether the test subject is in the mood disorder state based on the electroencephalograms occurring when the test subject is reliably in the sleep state (any of stages 2 to 4). Note that the stage discrimination part can discriminate the sleep stage using various biological signals such as an electroencephalogram, an electrooculogram, and an electromyogram of the test subject.

The comparison part may transform the first electroencephalogram into a frequency component to generate a first electroencephalogram spectrum, transform the second electroencephalogram into a frequency component to generate a second electroencephalogram spectrum, and compare an integral value of the first electroencephalogram spectrum in the specific frequency band with an integral value of the second electroencephalogram spectrum in the specific frequency band.

It is possible to compare the power of the first electroencephalogram with that of the second electroencephalogram in the specific frequency band by comparing the integral value of the first electroencephalogram spectrum with that of the second electroencephalogram spectrum in the specific frequency band, the first electroencephalogram spectrum and the second electroencephalogram spectrum being obtained by transforming the first electroencephalogram and the second electroencephalogram into frequency components, respectively.

The electroencephalogram analysis apparatus may further include a diagnosis part configured to diagnose whether the test subject is in a mood disorder state based on a comparison result of the comparison part.

The diagnosis part may diagnose that the test subject is in the mood disorder state when the power of the first electroencephalogram in the specific frequency band is greater than that of the second electroencephalogram in the specific frequency band.

An electroencephalogram analysis program according to another embodiment of the present disclosure causes a computer to function as an electroencephalogram acquisition part and a comparison part.

The electroencephalogram acquisition part is configured to acquire a first electroencephalogram measured at a first region on a head of a test subject and a second electroencephalogram measured at a second region positioned behind the first region on the head of the test subject.

The comparison part is configured to compare a power of the first electroencephalogram in a specific frequency band with a power of the second encephalogram in the specific frequency band.

An electroencephalogram analysis method according to still another embodiment of the present disclosure includes: acquiring a first electroencephalogram measured at a first region on a head of a test subject and a second electroencephalogram measured at a second region positioned behind the first region on the head of the test subject; and comparing a power of the first electroencephalogram in a specific frequency band with a power of the second encephalogram in the specific frequency band.

As described above, according to the embodiments of the present disclosure, it is possible to provide an electroencephalogram analysis apparatus, an electroencephalogram analysis program, and an electroencephalogram analysis method capable of diagnosing mood disorders based on the electroencephalograms of a test subject.

These and other objects, features and advantages of the present disclosure will become more apparent in light of the following detailed description of best mode embodiments thereof, as illustrated in the accompanying drawings.

BRIEF DESCRIPTION OF DRAWINGS

FIG. 4 is a table showing an example of the method of discriminating sleep stages;

FIGS. 9A and 9B are graphs respectively showing the distribution of the powers of the electroencephalograms (fast sleep spindles) measured at the measurement regions when the test subject is in the mood disorder state and the normal state.

DETAILED DESCRIPTION OF EMBODIMENTS (Configuration of Electroencephalogram Analysis Apparatus)

Figure 1:
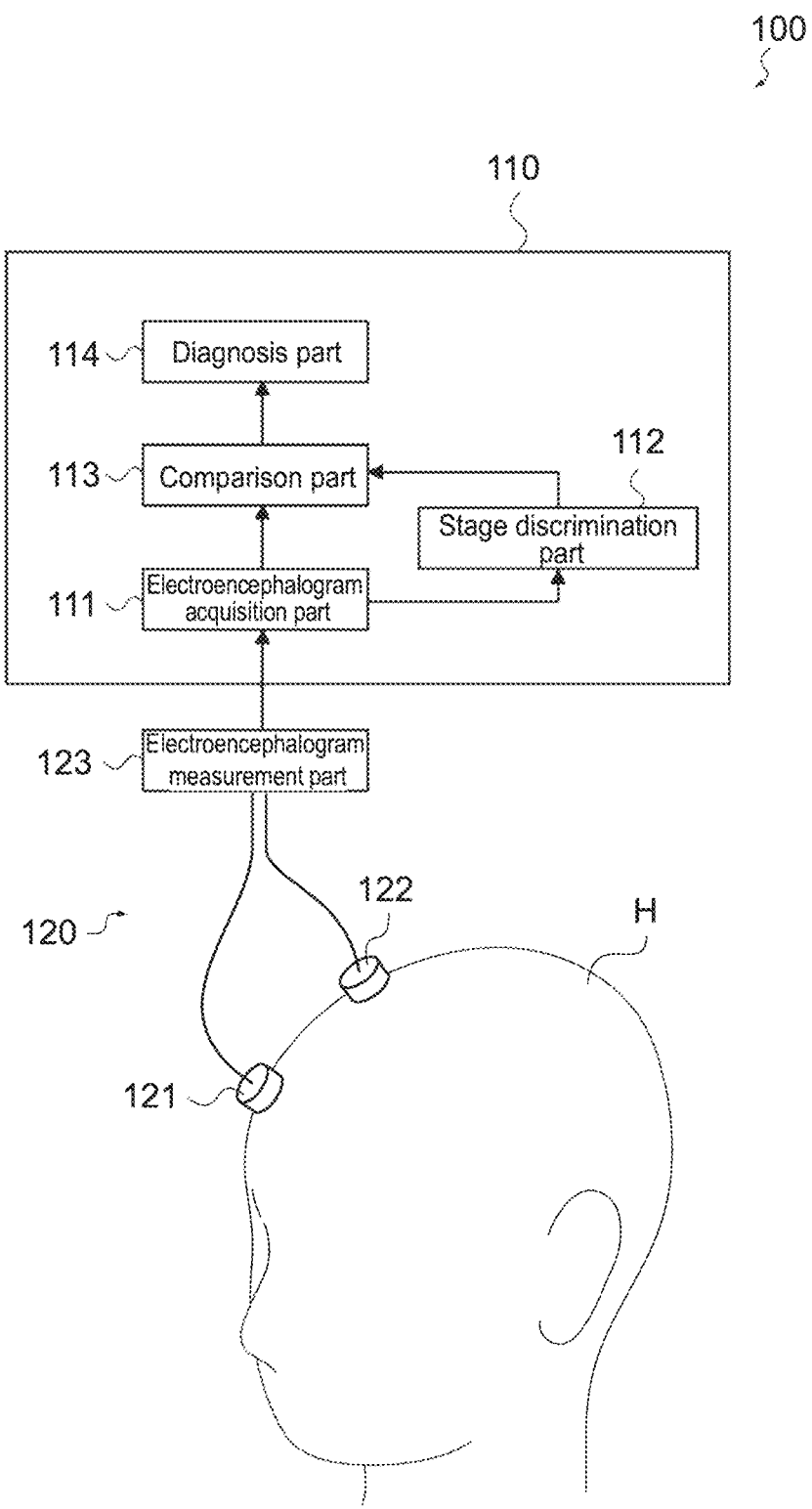
FIG. 1 is a schematic view showing an electroencephalogram analysis apparatus according to an embodiment of the present disclosure.

An electroencephalogram analysis apparatus according to an embodiment will be described. FIG. 1 is a schematic view showing the configuration of the electroencephalogram analysis apparatus 100. As shown in FIG. 1, the electroencephalogram analysis apparatus 100 includes an analysis unit 110 and an electroencephalograph 120. The analysis unit 110 is, for example, an information processing apparatus and connected to the electroencephalograph 120 to analyze electroencephalograms measured by the electroencephalograph 120. The analysis unit 110 and the electroencephalograph 120 may be integrated with each other or may be separated from each other. Further, FIG. 1 shows the head H of a test subject.

The electroencephalograph 120 includes a first measurement electrode 121, a second measurement electrode 122, and an electroencephalogram measurement part 123. The first measurement electrode 121 is connected to a "first region" on the head H to detect the electroencephalogram (EEG) of the test subject at the first region. The second measurement electrode 122 is connected to a "second region" on the head H to detect the electroencephalogram of the test subject at the second region. Note that the electroencephalograph 120 may further include, besides the first measurement electrode 121 and the second measurement electrode 122, a measurement electrode that detects the electroencephalogram.

Figure 2:
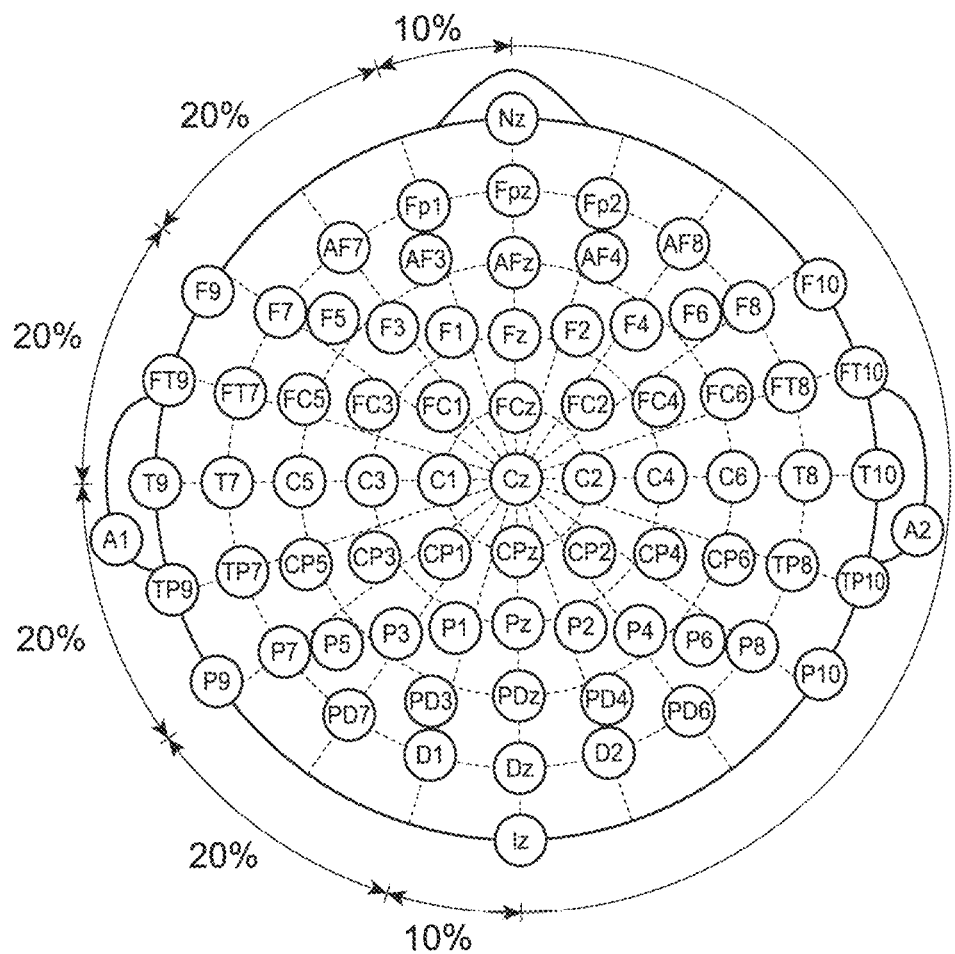
FIG. 2 is a schematic view of the measurement positions of electroencephalograms defined based on the International 10-20 system.

FIG. 2 is a schematic view for explaining the first region and the second region. Note that FIG. 2 shows the positions of measurement electrodes based on the International 10-20 system where the measurement positions of electroencephalograms are defined.

As will be described in detail below, the first region to which the first measurement electrode 121 is connected and the second region to which the second measurement electrode 122 is connected can be arranged such that the second region is positioned behind the first region in the head H of the test subject. More desirably, the first region can be a prefrontal region, and the prefrontal region corresponds to the Fp region (Fp1, Fpz, or Fp2) based on the International 10-20 system shown in FIG. 2.

Further, the second region can be a frontal region, and the frontal region corresponds to the F region (Fz or F1 to F9) based on the International 10-20 system shown in FIG. 2. Note that the first region and the second region are not necessarily the regions defined based on the International 10-20 system and only need to be regions at which a difference in the distribution of the powers of the electroencephalograms, which will be described below, can be measured.

The electroencephalogram measurement part 123 is connected to the first measurement electrode 121 and the second measurement electrode 122, measures the electroencephalograms detected by the first measurement electrode 121 and the second measurement electrode 122, and outputs the measured electroencephalograms to the analysis unit 110 in a wired or wireless manner. Hereinafter, the electroencephalogram measured by the first measurement electrode 121 at the first region will be referred to as a "first electroencephalogram," while the electroencephalogram measured by the second measurement electrode 122 at the second region will be referred to as a "second electroencephalogram." Note that the electroencephalograph 120 can further include a standard electrode (neutral electrode) that detects a standard potential of the electroencephalogram, a reference electrode that detects the contact resistance between the first and second measurement electrodes 121 and 122 and the front surface of the head H, or the like.

The analysis unit 110 includes an electroencephalogram acquisition part 111, a stage discrimination part 112, a comparison part 113, and a diagnosis part 114. These constituent parts can be functional parts implemented by the cooperation between the software and the hardware of the analysis unit 110 and may also be mounted on a network. The electroencephalogram acquisition part 111 is connected to the stage discrimination part 112 and the comparison part 113, and the comparison part 113 is connected to the diagnosis part 114. The stage discrimination part 112 is connected to the comparison part 113.

The electroencephalogram acquisition part 111 acquires the first electroencephalogram and the second electroencephalogram output from the electroencephalogram measurement part 123 of the electroencephalograph 120 and supplies the acquired first and second electroencephalograms to the stage discrimination part 112 and the comparison part 113.

The stage discrimination part 112 discriminates the "sleep stages" (see FIG. 4) of the test subject based on the first electroencephalogram and the second electroencephalogram supplied from the electroencephalogram acquisition part 111 or based on other measurement data on the test subject. In the sleep stages, the state of the test subject is classified into five stages 1 to 5 with a wakeful state as the first stage depending on the degree of the activity of the brain of the test subject. The sleep stages will be described in detail below. The stage discrimination part 112 supplies the discriminated sleep stage to the comparison part 113.

The comparison part 113 compares the power of the first electroencephalogram with that of the second electroencephalogram in a specific frequency band. The comparison part 113 can perform the comparison when the sleep stage of the test subject discriminated by the stage discrimination part 112 is any of the sleep states (stages 2 to 4). As the specific frequency band used by the comparison part 113 for the comparison, a frequency band (generally 10.5 Hz to 12.5 Hz) of sleep spindles, desirably, slow sleep spindles is available. The comparison part 113 supplies the comparison result to the diagnosis part 114.

Based on the comparison result of the comparison part 113, the diagnosis part 114 diagnoses whether the test subject has a mood disorder. Specifically, if the power of the first electroencephalogram is greater than that of the second electroencephalogram in the specific frequency band, the diagnosis part 114 can diagnose that the test subject is in the mood disorder state. On the other hand, if the power of the second electroencephalogram is greater than that of the first electroencephalogram in the specific frequency band, the diagnosis part 114 can diagnose that the test subject is not in the mood disorder state (the test subject is in a normal state). The diagnosis part 114 can display the diagnosis result on a display (not shown) or the like. Note that the mood disorder state refers to an abnormal mental state such as depression, schizophrenia, and bipolar disorder (symptom where a depressed state and a manic state alternately appear).

(Operations of Electroencephalogram Analysis Apparatus)

Figure 3:
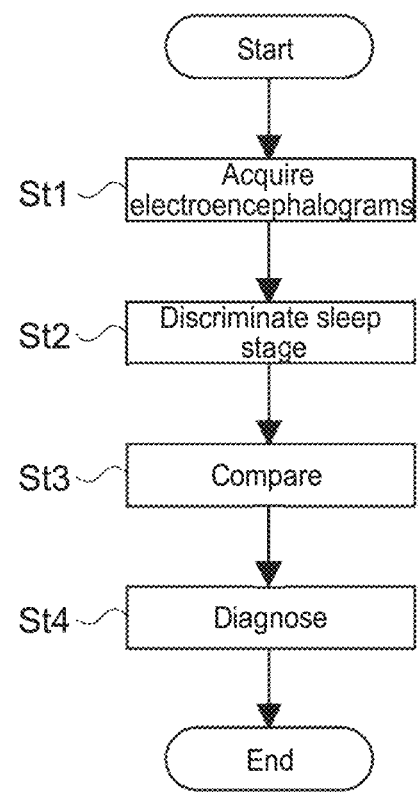
FIG. 3 is a flowchart showing the operations of the electroencephalogram analysis apparatus according to the embodiment of the present disclosure.

The operations of the electroencephalogram analysis apparatus 100 will be described. FIG. 3 is a flowchart showing the operations of the electroencephalogram analysis apparatus 100.

The electroencephalogram acquisition part 111 acquires the first electroencephalogram and the second electroencephalogram from the electroencephalogram measurement part 123 (Step 1). The electroencephalogram acquisition part 111 may acquire the first electroencephalogram and the second electroencephalogram from the electroencephalogram measurement part 123 as occasion demands, or is capable of acquiring the first electroencephalogram and the second electroencephalogram measured by the electroencephalogram measurement part 123 and recorded on a recording part (not shown) for a predetermined period of time. The electroencephalogram acquisition part 111 supplies the first electroencephalogram and the second electroencephalogram thus acquired to the stage discrimination part 112 and the comparison part 113.

Next, the stage discrimination part 112 discriminates the sleep stage of the test subject (Step 2). FIG. 4 is a table showing the respective sleep stages and an example of the method of discriminating the sleep stages. As shown in FIG. 4, the sleep state of the test subject can be classified into any of the non-sleep stage (WAKE), the REM sleep stage (REM), and the non-REM sleep stage depending on the state of the activity of the brain. In the case of the non-REM sleep stage, the sleep state of the test subject can further be classified into any of the stage 1 (hypnagogic state), the stage 2 (light sleep state), the stage 3 (moderate sleep state), and the stage 4 (deep sleep state) depending on the depth of the sleep of the test subject.

The stage discrimination part 112 discriminates which of the sleep stages the sleep state of the test subject is classified into. The stage discrimination part 112 may discriminate the sleep stages using the first electroencephalogram and the second electroencephalogram supplied from the electroencephalogram acquisition part 111, or may discriminate the sleep stages using other biological signals obtained by measuring the test subject. As the biological signals, an electrooculogram (EGO), an electromyogram (EMG), or the like is available. The stage discrimination part 112 supplies the discriminated sleep stage to the comparison part 113.

Then, the comparison part 113 compares the power of the first electroencephalogram with that of the second electroencephalogram in the specific frequency band (Step 3). Here, the comparison part 113 can perform the comparison only when the sleep stage discriminated by the stage discrimination part 112 is any of the sleep stages 2 to 4. This is because, when the test subject is in the incomplete sleep states (WAKE, REM, and stage 1), electroencephalograms (such as alpha waves) whose frequency band overlaps with the specific frequency band may occur, i.e., the diagnosis of the diagnosis part 114 (that will be described below) may be inhibited.

Figure 5A:
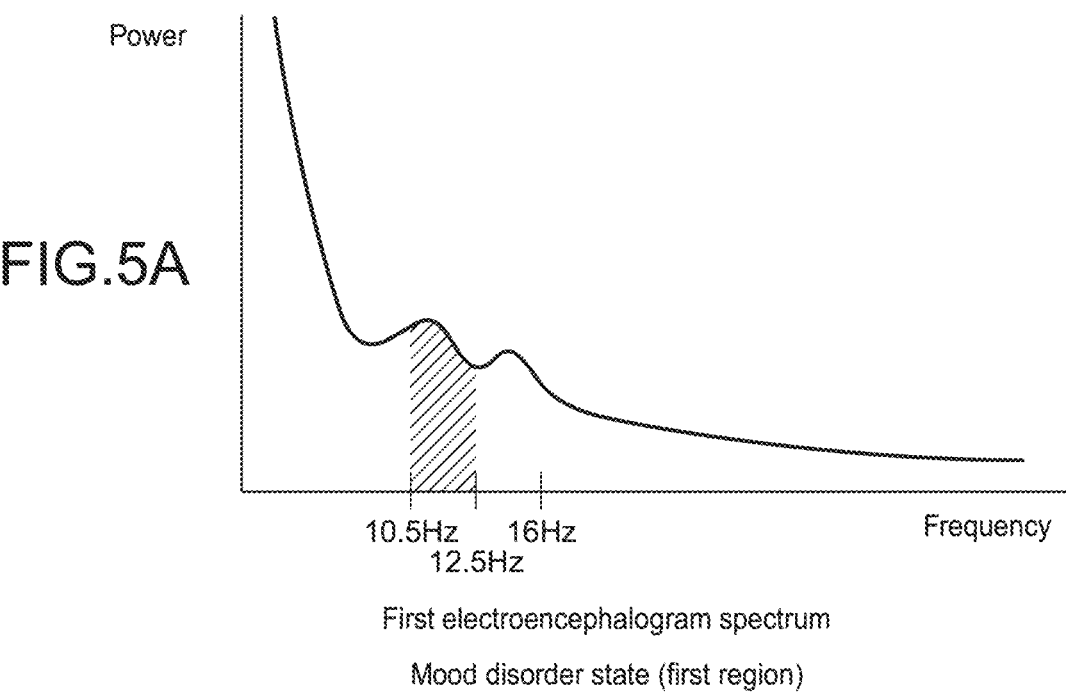
FIGS. 5A and 5B are graphs showing the examples of electroencephalogram spectrums generated by the electroencephalogram analysis apparatus according to the embodiment of the present disclosure.
Figure 5B:
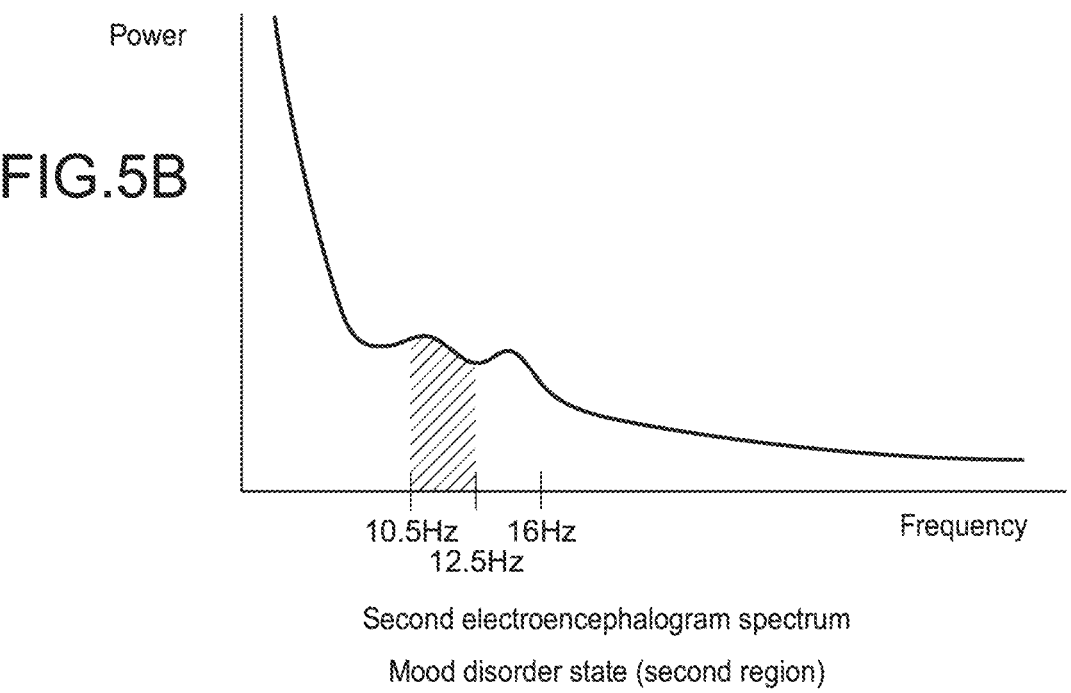

The comparison part 113 can perform the comparison by transforming (frequency-transforming) the first electroencephalogram and the second electroencephalogram into frequency components. Hereinafter, the frequency component transformed from the first electroencephalogram will be referred to as a first electroencephalogram spectrum, while the frequency component transformed from the second electroencephalogram will be referred to as a second electroencephalogram spectrum. FIGS. 5A and 5B are graphs showing the examples of the first electroencephalogram spectrum and the second electroencephalogram spectrum, respectively. The comparison part 113 can frequency-transform the first electroencephalogram and the second electroencephalogram according to any method, for example, a fast Fourier transform, a wavelet transform, or the like.

Using the first electroencephalogram spectrum and the second electroencephalogram spectrum, the comparison part 113 can compare the power of the first electroencephalogram with that of the second electroencephalogram in the specific frequency band. Specifically, the comparison part 113 can compare the integral value of the first electroencephalogram spectrum in the specific frequency band (here, greater than or equal to 10.5 Hz and less than or equal to 12.5 Hz) with that of the second electroencephalogram spectrum in the specific frequency band. In FIGS. 5A and 5B, the integral values of the first electroencephalogram spectrum and the second electroencephalogram spectrum in the specific frequency band (greater than or equal to 10.5 Hz and less than or equal to 12.5 Hz) are indicated as the areas of shaded regions.

As the specific frequency band, a frequency band (greater than or equal to 10.5 Hz and less than or equal to 16 Hz) of sleep spindles can be set. Further, the sleep spindles can be classified into fast sleep spindles (greater than or equal to 12.5 Hz and less than or equal to 16 Hz) and slow sleep spindles (greater than or equal to 10.5 Hz and less than or equal to 12.5 Hz). However, the frequency band of the slow sleep spindles (that will be described below) is particularly desirable as the specific frequency band. Note that the specific numerical values (such as 10.5 Hz) exemplified here as the frequency band are the numerical values generally used in the field of electroencephalogram measurement, and the specific frequency band is not necessarily limited to the values.

As shown in FIGS. 5A and 5B, the comparison part 113 can compare the power of the first electroencephalogram with that of the second electroencephalogram in the specific frequency band by comparing the size of the integral value of the first electroencephalogram spectrum with that of the second electroencephalogram spectrum in the specific frequency band. Further, the comparison part 113 does not necessarily use the electroencephalogram spectrums and is capable of comparing the power of the first electroencephalogram with that of the second electroencephalogram in the specific frequency band according to other methods. The comparison part 113 supplies the comparison result, i.e., the relationship between the power of the first electroencephalogram and that of the second electroencephalogram in the specific frequency band to the diagnosis part 114.

The diagnosis part 114 diagnoses whether the test subject is in the mood disorder state based on the comparison result of the comparison part 113 (Step 4). The diagnosis part 114 can diagnose that the test subject is in the mood disorder state if the comparison result of the comparison part 113 shows that the power of the first electroencephalogram is greater than that of the second electroencephalogram in the specific frequency band. On the other hand, the diagnosis part 114 can diagnose that the test subject is not in the mood disorder state (the test subject is in the normal state) if the comparison result of the comparison part 113 shows that the power of the first electroencephalogram is less than that of the second electroencephalogram in the specific frequency band. For example, because FIGS. 5A and 5B show a case where the power of the first electroencephalogram (the area of the shaded region in FIG. 5A) is greater than that of the second electroencephalogram (the area of the shaded region in FIG. 5B) in the specific frequency band (greater than or equal to 10.5 Hz and less than or equal to 12.5 Hz), the diagnosis part 114 can diagnose that the test subject is in the mood disorder state.

Figure 6A:
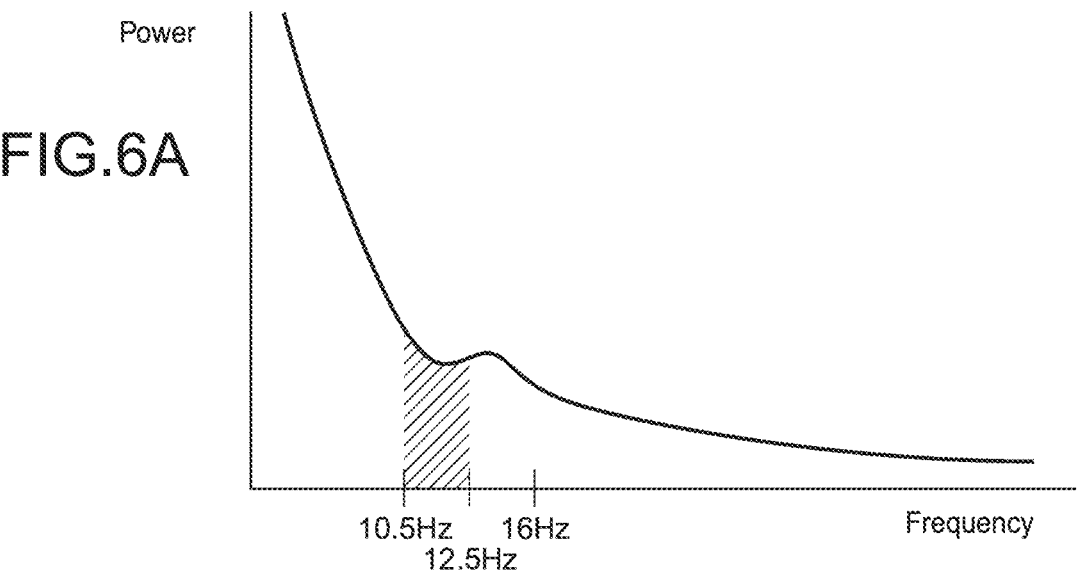
FIGS. 6A and 6B are graphs showing the examples of electroencephalogram spectrums generated by the electroencephalogram analysis apparatus according to the embodiment of the present disclosure.
Figure 6B:
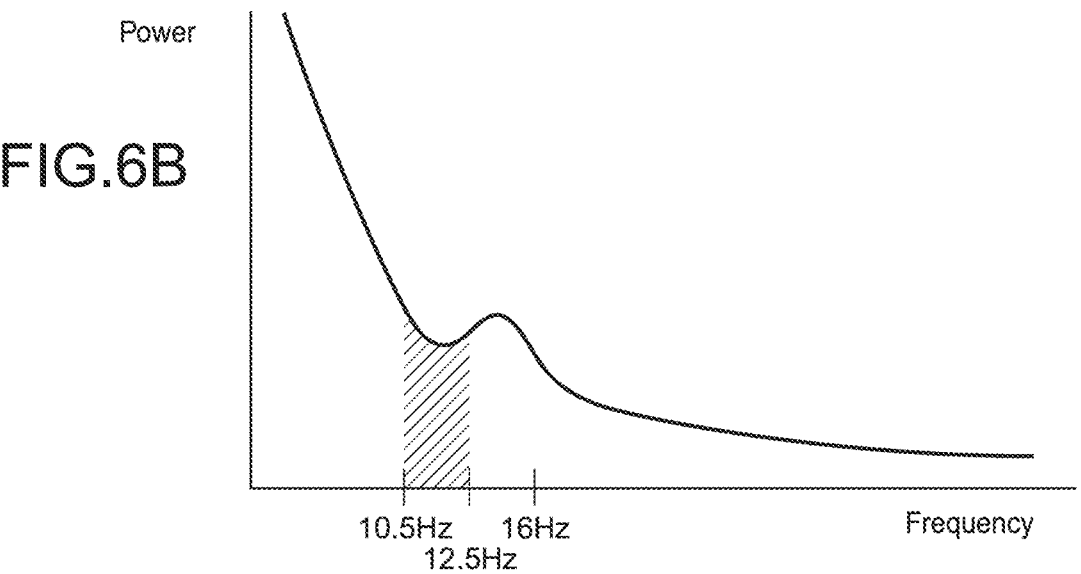

On the other hand, FIGS. 6A and 6B are graphs showing the examples of the first electroencephalogram spectrum acquired at the first region and the second electroencephalogram spectrum acquired at the second region, respectively. Because the power of the first electroencephalogram (the area of the shaded region in FIG. 6A) is less than that of the second electroencephalogram (the area of the shaded region in FIG. 6B) in the specific frequency band (greater than or equal to 10.5 Hz and less than or equal to 12.5 Hz), the diagnosis part 114 can diagnose that the test subject is in the normal state.

(Principle of Diagnosis)

Figure 7A:
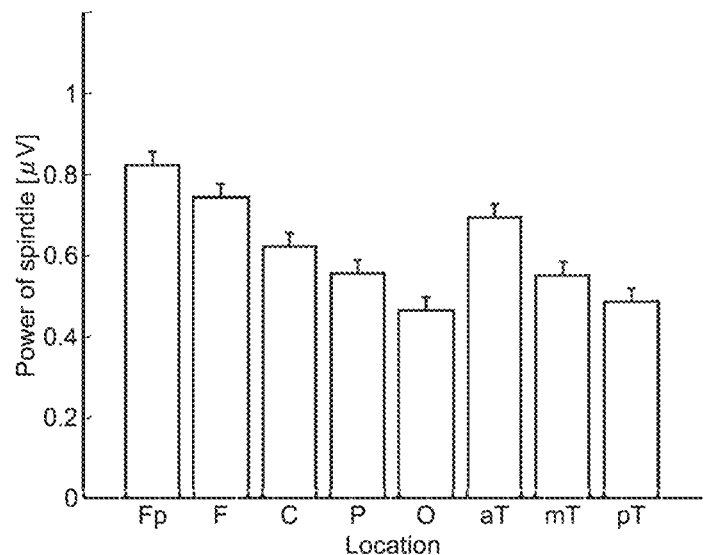
FIGS. 7A and 7B are graphs respectively showing the powers of the electroencephalograms (slow sleep spindles) measured at the measurement regions when a test subject is in a mood disorder state and a normal state.
Figure 7B:
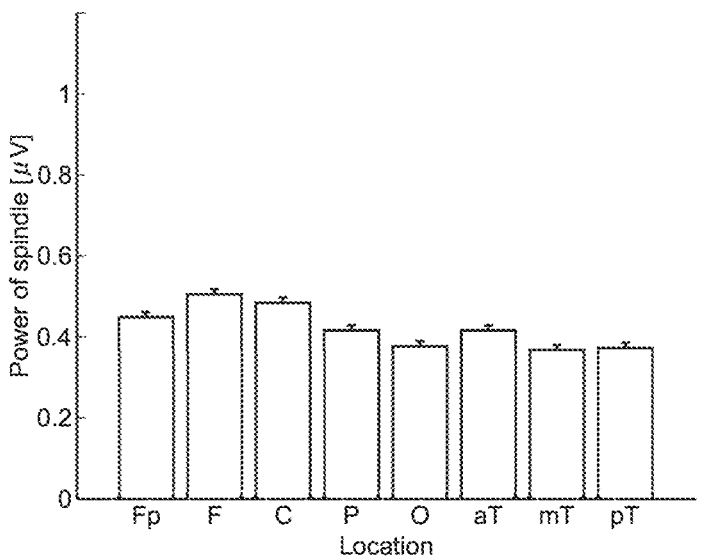

The principle by which the diagnosis part 114 can perform the above diagnosis will be described. FIGS. 7A and 7B are graphs showing the powers of the slow sleep spindles (greater than or equal to 10.5 Hz and less than or equal to 12.5 Hz) measured at the respective regions of the head of the test subject. FIG. 7A shows the powers of the slow sleep spindles obtained when the test subject in the mood disorder state is measured, while FIG. 7B shows the powers of the slow sleep spindles obtained when the test subject in the normal state is measured. The graphs shown in FIGS. 7A and 7B are obtained in such a manner that the respective regions based on the International 10-20 system shown in FIG. 2 are measured. The comparison between these graphs shows that the power of the slow sleep spindle at the prefrontal region (the Fp region) is the greatest in the graph shown in FIG. 7A, while the power of the slow sleep spindle at the frontal region (the F region) is the greatest in the graph shown in FIG. 7B.

Figure 8A:
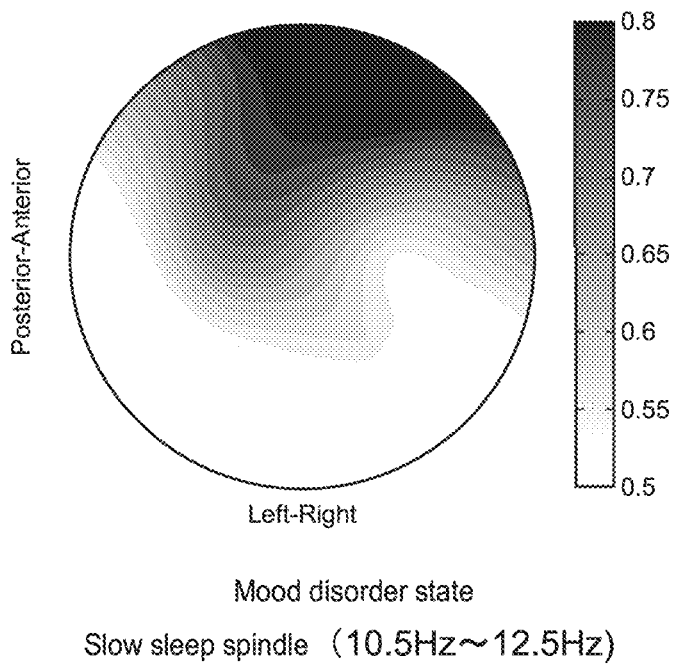
FIGS. 8A and 8B are schematic views respectively showing the distribution of the powers of the electroencephalograms (slow sleep spindles) measured at the measurement regions when the test subject is in the mood disorder state and the normal state.
Figure 8B:
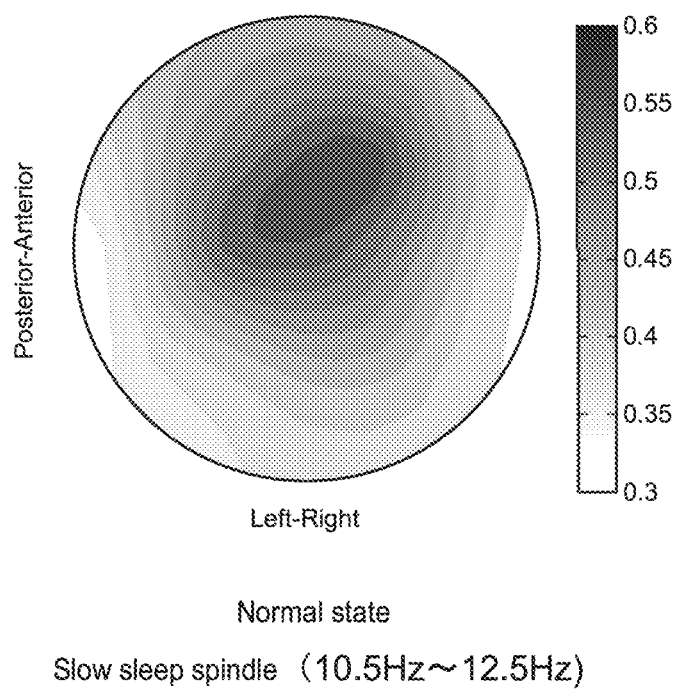

FIGS. 8A and 8B each display the distribution of the powers of the slow sleep spindles measured at the respective regions so as to be reflected in the shape of the head of the test subject (the upper side of the head in each of FIGS. 8A and 8B represents the front side of the test subject). FIG. 8A shows the distribution of the powers of the slow sleep spindles measured when the test subject is in the mood disorder state, while FIG. 8B shows the distribution of the powers of the slow sleep spindles measured when the test subject is in the normal state. In FIGS. 8A and 8B, the greater the powers of the slow sleep spindles, the darker the regions are colorized. It is found that, when the test subject is in the mood disorder state, the regions of the greater powers of the slow sleep spindles exist on the front side of the head (near the prefrontal region) as shown in FIG. 8A. On the other hand, it is found that, when the test subject is in the normal state, the regions of the greater powers of the slow sleep spindles exist on a further rear side of the head (near the frontal region) as shown in FIG. 8B.

Accordingly, it is possible to diagnose whether the test subject is in the mood disorder state by the comparison of the powers of the electroencephalograms between the first region (for example, the prefrontal region) and the second region (for example, the frontal region) positioned on the further rear side of the head of the test subject in the frequency band of the slow sleep spindles. As shown in FIGS. 7A and 8A, when the test subject is in the mood disorder state, the powers of the electroencephalograms on the front side of the head become greater. Accordingly, when the power (the area of the shaded region) of the electroencephalogram of the first region (first electroencephalogram) shown in FIG. 5A is compared with that (the area of the shaded region) of the electroencephalogram of the second region (second electroencephalogram) shown in FIG. 5B, it is found that the power of the electroencephalogram of the first region (FIG. 5A) is greater than that of the electroencephalogram of the second region (FIG. 5B).

On the other hand, as shown in FIGS. 7B and 8B, when the power of the electroencephalogram of the first region (first electroencephalogram) is compared with that of the electroencephalogram of the second region (second electroencephalogram) as for the test subject in the normal state, it is found that the power of the second electroencephalogram is greater than that of the first electroencephalogram. As shown in FIGS. 7B and 8B, when the test subject is in the normal state, the powers of the electroencephalograms become greater near the center of the head. Accordingly, when the power (the area of the shaded region) of the electroencephalogram of the first region (first electroencephalogram) shown in FIG. 6A is compared with that (the area of the shaded region) of the electroencephalogram of the second region (second electroencephalogram) shown in FIG. 6B, it is found that the power of the electroencephalogram of the second region (FIG. 6B) is greater than that of the electroencephalogram of the first region (FIG. 6A).

As described above, using the difference in the distribution of the powers of the slow sleep spindles between the mood disorder state and the normal state, it is possible to diagnose whether the test subject is in the mood disorder state based on the power of the first electroencephalogram measured at the first region and that of the second electroencephalogram measured at the second region.

In the above description, the frequency band (for example, greater than or equal to 10.5 Hz and less than or equal to 12.5 Hz) of the slow sleep spindles is set as the specific frequency band for use in the diagnosis of the diagnosis part 114. However, the specific frequency band is not limited to the frequency band of the slow sleep spindles. Any specific frequency bands showing the same tendency as that of the slow sleep spindles can be set as the specific frequency band for use in the diagnosis. Hereinafter, a description will be given of a case where the frequency band (for example, greater than or equal to 12.5 Hz and less than or equal to 16 Hz) of the fast sleep spindles is set as the specific frequency band.

FIGS. 9A and 9B are graphs showing the powers of the fast sleep spindles measured at the respective regions of the head of the test subject. FIG. 9A shows the powers of the fast sleep spindles obtained when the test subject in the mood disorder state is measured, while FIG. 9B shows the powers of the fast sleep spindles obtained when the test subject in the normal state is measured. The graphs shown in FIGS. 9A and 9B are obtained in such a manner that the respective regions based on the International 10-20 system shown in FIG. 2 are measured. The comparison between these graphs shows that the power of the fast sleep spindle at the frontal region (the F region) is the greatest in the graph shown in FIG. 9A, while the power of the fast sleep spindle at the top of the head (the C region) is the greatest in the graph shown in FIG. 9B.

Figure 10A:
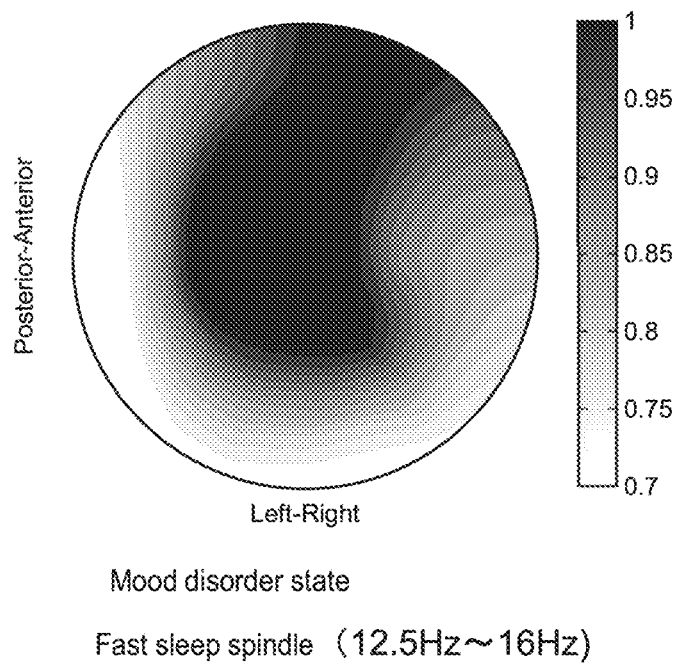
FIGS. 10A and 10B are schematic views respectively showing the distribution of the powers of the electroencephalograms (fast sleep spindles) measured at the measurement regions when the test subject is in the mood disorder state and the normal state.
Figure 10B:
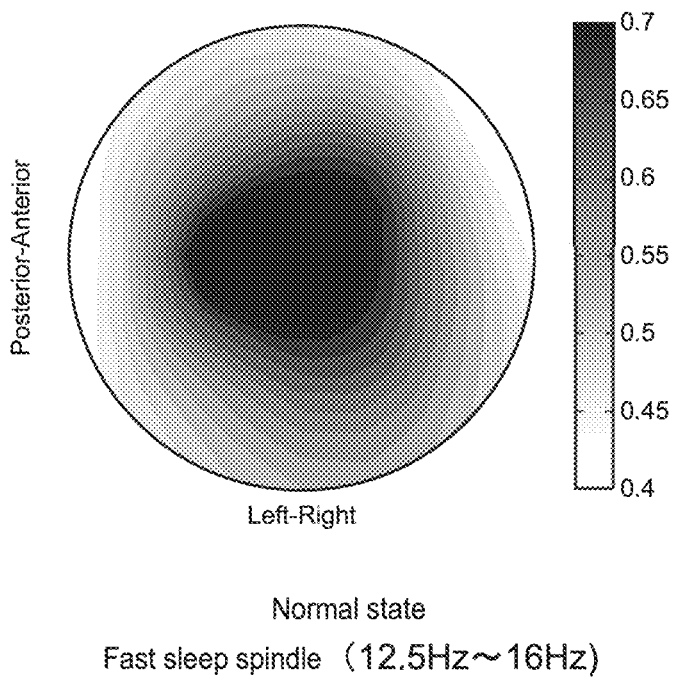

FIGS. 10A and 10B each display the distribution of the powers of the fast sleep spindles measured at the respective regions so as to be reflected in the shape of the head of the test subject (the upper side of the head in each of FIGS. 10A and 10B represents the front side of the test subject). FIG. 10A shows the distribution of the powers of the fast sleep spindles measured when the test subject is in the mood disorder state, while FIG. 10B shows the distribution of the powers of the fast sleep spindles measured when the test subject is in the normal state. In FIGS. 10A and 10B, the greater the powers of the fast sleep spindles, the darker the regions are colorized. It is found that, when the test subject is in the mood disorder state, the regions of the greater powers of the fast sleep spindles exist on the front side of the head (near the prefrontal region) as shown in FIG. 10A. On the other hand, it is found that, when the test subject is in the normal state, the regions of the greater powers of the fast sleep spindles exist on a further rear side of the head (near the frontal region) as shown in FIG. 10B.

Accordingly, similar to the case where the frequency band of the slow sleep spindles is set as the specific frequency band, it is possible to diagnose whether the test subject is in the mood disorder state or the normal state by setting the frequency band of the fast sleep spindles as the specific frequency band. Specifically, when the test subject is in the mood disorder state, the power of the first electroencephalogram (FIG. 5A) becomes greater in the frequency band (greater than or equal to 12.5 Hz and less than or equal to 16 Hz) of the fast sleep spindles as shown in FIGS. 5A and 5B. On the other hand, when the test subject is in the normal state, the power of the second electroencephalogram (FIG. 6B) becomes greater in the same frequency band of the fast sleep spindles as shown in FIGS. 6A and 6B. In other words, using the frequency band of the fast sleep spindles, it is possible to diagnose whether the test subject is in the mood disorder state or the normal state by the comparison between the power of the first electroencephalogram and that of the second electroencephalogram.

Further, when the test subject is in the mood disorder state, the comparison between the distribution of the powers of the slow sleep spindles shown in FIG. 8A and that of the powers of the fast sleep spindles shown in FIG. 10A shows that the existence of the regions of the greater powers on the front side of the head can be notably seen in the slow sleep spindles (FIG. 8A and FIG. 10A). Accordingly, it seems to be possible to more clearly diagnose whether the test subject is in the mood disorder state or the normal state by setting the frequency band of the slow sleep spindles as the specific frequency band for use in the diagnosis.

Note that the difference in the distribution of the powers of the sleep spindles between the mood disorder state and the normal state is assumed to be caused by the malfunction of a thalamofrontal circuit in the mood disorder state. It is suggested that the thalamofrontal circuit related to the rostal reticular and the mediodorsal nucleus of a thalamus interferes with the sleep spindles of about 12 Hz.

As described above, based on the difference in the distribution of the powers of the electroencephalograms in the specific frequency band between the mood disorder state and the normal state, it is possible to diagnose whether the test subject is in the mood disorder state or the normal state. The first measurement electrode 121 and the second measurement electrode 122 are arranged at the regions at which the difference in the distribution of the powers can be detected. Specifically, the first region at which the first measurement electrode is arranged and the second region at which the second measurement electrode 122 is arranged can be set such that the first region and the second region are on the front and rear sides of the head H of the test subject, respectively. More specifically, the first region can be set as the prefrontal region (the Fp region based on the International 10-20 system), while the second region can be set as the frontal region (the F region based on the International 10-20 system).

As the specific frequency band for use in the diagnosis, the frequency band (generally 10.5 Hz to 16 Hz) of the sleep spindles can be set. Particularly, the frequency band (generally 10.5 Hz to 12.5 Hz) of the slow sleep spindles is effective because the difference in the distribution of the powers can be notably seen. Note that the specific frequency band is not limited to the frequency band of the sleep spindles, and any frequency bands are available so long as the difference in the distribution of the powers between the mood disorder state and the normal state can be seen in the frequency bands.

As described above, using the electroencephalogram analysis apparatus 100 according to the embodiment, it is possible to provide an objective barometer indicating whether the test subject is in the mood disorder state or the normal state. Because it is only necessary for the test subject to be in a sleep state and only a small burden is placed on the test subject to perform the diagnosis, the present disclosure is also applicable to home monitoring.

The present disclosure is not limited to the above respective embodiments but can be modified without departing from the spirit of the present disclosure.

Note that the present disclosure may also employ the following configurations.

(1) An electroencephalogram analysis apparatus, including:

an electroencephalogram acquisition part configured to acquire a first electroencephalogram measured at a first region on a head of a test subject and a second electroencephalogram measured at a second region positioned behind the first region on the head of the test subject; and a comparison part configured to compare a power of the first electroencephalogram in a specific frequency band with a power of the second encephalogram in the specific frequency band.

(2) The electroencephalogram analysis apparatus according to (1), in which the first region is a prefrontal region, and the second region is a frontal region.

(3) The electroencephalogram analysis apparatus according to (1) or (2), in which the first region is an Fp region defined based on the International 10-20 system, and the second region is an F region defined based on the International 10-20 system.

(4) The electroencephalogram analysis apparatus according to any one of (1) to (3), in which the specific frequency band is a frequency band of sleep spindles.

(5) The electroencephalogram analysis apparatus according to any one of (1) to (4), in which the specific frequency band is a frequency band of slow sleep spindles.

(6) The electroencephalogram analysis apparatus according to any one of (1) to (5), in which the frequency band of the slow sleep spindles is greater than or equal to 10.5 Hz and less than or equal to 12.5 Hz.

(7) The electroencephalogram analysis apparatus according to any one of (1) to (6), further including a stage discrimination part configured to discriminate a sleep stage of the test subject, in which the first electroencephalogram is an electroencephalogram of any of sleep stages 2 to 4 measured at the first region, and the second electroencephalogram is an electroencephalogram of any of the sleep stages 2 to 4 measured at the second region.

(8) The electroencephalogram analysis apparatus according to any one of (1) to (7), in which the comparison part transforms the first electroencephalogram into a frequency component to generate a first electroencephalogram spectrum, transforms the second electroencephalogram into a frequency component to generate a second electroencephalogram spectrum, and compares an integral value of the first electroencephalogram spectrum in the specific frequency band with an integral value of the second electroencephalogram spectrum in the specific frequency band.

(9) The electroencephalogram analysis apparatus according to any one of (1) to (8), further including:

a diagnosis part configured to diagnose whether the test subject is in a mood disorder state based on a comparison result of the comparison part.

(10) The electroencephalogram analysis apparatus according to any one of (1) to (9), in which
the diagnosis part diagnoses that the test subject is in the mood disorder state when the power of the first electroencephalogram in the specific frequency band is greater than the power of the second electroencephalogram in the specific frequency band.

(11) An electroencephalogram analysis program that causes a computer to function as:
an electroencephalogram acquisition part configured to acquire a first electroencephalogram measured at a first region on a head of a test subject and a second electroencephalogram measured at a second region positioned behind the first region on the head of the test subject; and
a comparison part configured to compare a power of the first electroencephalogram in a specific frequency band with a power of the second encephalogram in the specific frequency band.

(12) An electroencephalogram analysis method, including:
acquiring a first electroencephalogram measured at a first region on a head of a test subject and a second electroencephalogram measured at a second region positioned behind the first region on the head of the test subject; and
comparing a power of the first electroencephalogram in a specific frequency band with a power of the second encephalogram in the specific frequency band.

The present disclosure contains subject matter related to that disclosed in Japanese Priority Patent Application JP 2012-086588 filed in the Japan Patent Office on Apr. 5, 2012, the entire content of which is hereby incorporated by reference.

What is claimed is:

1. An electroencephalogram analysis apparatus, comprising:
    circuitry configured to:
        obtain a first electroencephalogram at a first region on a head of a test subject and a second electroencephalogram at a second region that is behind the first region on the head of the test subject;
        determine the test subject is in a sleeping state based on the obtained first electroencephalogram and the obtained second electroencephalogram;
        compare a first power of the obtained first electroencephalogram in a specific frequency band with a second power of the obtained second electroencephalogram in the specific frequency band, wherein the comparison is based on the determination the test subject is in the sleeping state; and
        output, based on a result of the comparison, an estimation result that indicates a state of the test subject is at least one of normal, depression, schizophrenia, or bipolar disorder.

2. The electroencephalogram analysis apparatus according to claim 1, wherein the circuitry is further configured to estimate the state of the test subject is at least one of depression, schizophrenia, or bipolar disorder based on the first power that is greater than the second power.

3. The electroencephalogram analysis apparatus according to claim 1, wherein the circuitry is further configured to determine the sleeping state of the test subject based on the first electroencephalogram and the second electroencephalogram that include delta waves.

4. The electroencephalogram analysis apparatus according to claim 3, wherein the specific frequency band is a frequency band of sleep spindles.

5. The electroencephalogram analysis apparatus according to claim 4, wherein the specific frequency band corresponds to one of a frequency band of slow sleep spindles or a frequency band of fast sleep spindles.

6. The electroencephalogram analysis apparatus according to claim 5, wherein
    the first region is an Fp region defined based on an International 10-20 system, and
    the second region is an F region defined based on the International 10-20 system.

7. The electroencephalogram analysis apparatus according to claim 4, wherein the specific frequency band is one of:
    greater than or equal to 10.5 Hz and less than or equal to 12.5 Hz, or
    greater than or equal to 12.5 Hz and less than or equal to 16 Hz.

8. The electroencephalogram analysis apparatus according to claim 1, wherein the circuitry is further configured to determine the sleeping state of the test subject based on at least one of electrooculogram data or electromyogram data.

9. An electroencephalogram analysis apparatus, comprising:
    circuitry configured to:
        obtain a first electroencephalogram at a first region on a head of a test subject and a second electroencephalogram at a second region that is behind the first region on the head of the test subject;
        determine the test subject is in a sleeping state based on the obtained first electroencephalogram and the obtained second electroencephalogram;
        compare a first power of the obtained first electroencephalogram in a specific frequency band with a second power of the obtained second electroencephalogram in the specific frequency band, wherein the comparison is based on the determination the test subject is in the sleeping state; and
        output, based on a result of the comparison, an estimation result that indicates a state of a thalamofrontal of the test subject is at least one of depression, bipolar disorder, or schizophrenia,
    wherein the result of the comparison indicates that the first power is greater than the second power.

* * * * *